US00PP07923P

United States Patent [19]

Feldman et al.

[11] Patent Number: Plant 7,923

[45] Date of Patent: Jul. 28, 1992

[54] APPLE TREE NAMED 'SPENCERVILLE RED'

[76] Inventors: Eugene P. Feldman, 1300 Paris Ridge Dr., Spencerville, Md. 20868; Carlton E. Heyser, Jr., 14526 New Hampshire Ave., Silver Spring, Md. 20904

[21] Appl. No.: 668,151

[22] Filed: Mar. 12, 1991

[51] Int. Cl.[5] ..... A01H 5/00

[52] U.S. Cl. ..... Plt./34.1

[58] Field of Search ..... Plt./34

*Primary Examiner*—James R. Feyrer

[57] ABSTRACT

A new and distinct variety of apple, the '*Spencerville Red*' was discovered growing from seed in a cultivated field in Spencerville, Md. The tree and fruit are similar in some respects to the York Imperial but the tree flowers and ripens about a week later. The fruit is hard, tart, and fine in texture.

1 Drawing Sheet

HISTORY OF THE VARIETY

This invention is a new and distinct variety of apple which grew from seed in a cultivated field in Spencerville, Md. The genetic extraction of this apple, which we call the 'Spencerville Red', is unknown; its likely antecedents are the York Imperial and a crab apple, both of which grow in our nearby orchard.

Subsequent to our discovery of this tree and a preliminary conclusion that its fruit exhibited a number of desirable characteristics, the tree was reproduced asexually by both budding and grafting onto M26 rootstock and by grafting on M26 rootstock with an interstem of Granny Smith. Several budded and grafted trees have been incorporated into an established commercial orchard for further observation and evaluation of the grown habits and fruiting behavior of this variety. The fruit produced by these trees is identical to that produced by the parent tree in all distinguishing characteristics.

BRIEF DESCRIPTION OF THE VARIOUS FIGURES INCLUDED IN THE DRAWINGS

The figure at the upper left shows the branching pattern of the moderately pruned parent tree.

The figure at the upper right shows the branching pattern of a 3 year old graft on M26 rootstock.

The figure in the middle shows the characteristic shape of the fruit and its skin color.

The figure at the lower left shows the fruit in longitudinal cross section.

The figure at the lower right shows the fruit in lattitudinal cross section.

The Tree

The growth habit of the tree itself is moderately vigorous on its own root upright with most branching producing crotch angles greater than 45 degrees, normally approaching 90 degrees. It is easily trainable to either a central leader or slender spindle type tree. Its height after ten years, with moderate dormant pruning over the last four years, is about sixteen feet. The leaves are typical of apple trees; gray-green, elliptic with an elongated point. Petioles are from 2 to 3 cm; the left blade is 6 to 8 cm. long and about 4 cm. wide with finely serrated fringes.

The tree has much in common with the York Imperial. The bark is grayish and similar to that of the York Imperial, the fruiting wood is similar in the number, size, and location of both leaf buds and fruiting spurs, and it is a biennial producer under natural conditions. Its white-pink, moderately sized flowers also resemble those of the 'York Imperial' but full bloom for the 'Spencerville Red' occurs between two and seven days after the full bloom for the 'York Imperial'. In 1987, 1988 and 1989, full bloom for the 'Spencerville Red' occurred in the last week in April. As the original tree is isolated but bears well, it is believed that the tree is self-pollinated. The tree shows resistance to fireblight; several grafted trees, surrounded by blighted 'Jonathan' and 'Paula Red' in an orchard, were unaffected.

The Fruit

The 'Spencerville Red' apple is bright red, with color covering 85-90% of the fruit at maturity. It has a brown-russet color explosion coming out from the stem area, similar to the 'Jonathan'. The fruit is somewhat lopsided in shape but not to the extent that characterizes the 'York' variety and its ripening date is about a week later than the 'York': in Spencerville being usually the last week in October.

The fruit has two unusual attributes: the flesh does not readily discolor when the apple is cut and exposed to the air and it maintains its structure when cooked. It is moderately juicy and has a distinctive tart flavor similar to that of a mellow crab apple or a very tart 'Jonathan'. The flesh is white but it is harder than the 'Jonathan' and has a finer texture. In conventional cold storage, it will retain its quality for five months or longer (stored at 33 degrees F.).

The following is a detailed description of this new apple:

Variety: 'Spencerville Red'.

Parentage: Believed to be a combination of 'York Imperial' and crab apple.

Tree: Moderately vigorous growth habit, blossoming in the last week in April; a biennial producer under natural conditions. Medium number and medium size of lenticels. Bark is gray and leaves are gray-green, typical of the species.

Fruit: Round-conical in shape; somewhat rhomboid, like the 'York', but taller from calyx end to stem end; about 70 to 75 mm high and 70 to 75 MM wide. It is not unusual for one half of the apple to be larger than the other so that the shape becomes trapezoidal. No beading or hammering. Flesh is hard and white with fine texture, and moderately juicy. Ripening is in the last week in October.

Eye: Smooth with a deep basin; open with a channel up to the central core.

Skin: Thin and slightly striped, with many small lenticels. The ground color, as identified by reference to the *Wilson Colour Chart* is Aureolin (3/2) with streaks of Chartreuse Green (663/2). The blush is Blood Red (820/1 or 820/2). There is little russeting.

Core: The core is oval, with core lines normal; similar to those of 'York'. Seeds are typical of the species with no observable distinctions.

Disease: Resistant to fireblight.

We claim:

1. A new and distinct variety of apple as described and illustrated above, a tree grown from seed in a cultivated field in Spencerville, Md. and named 'Spencerville Red'.

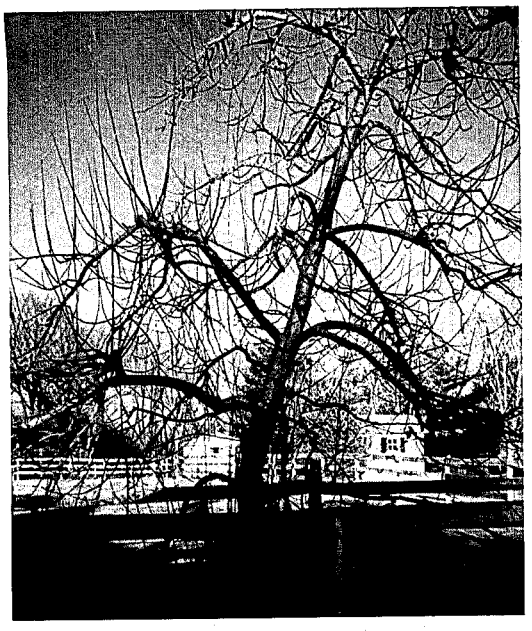
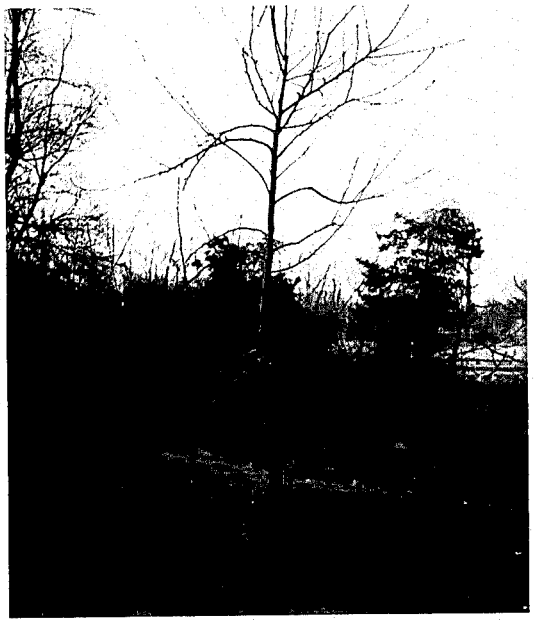
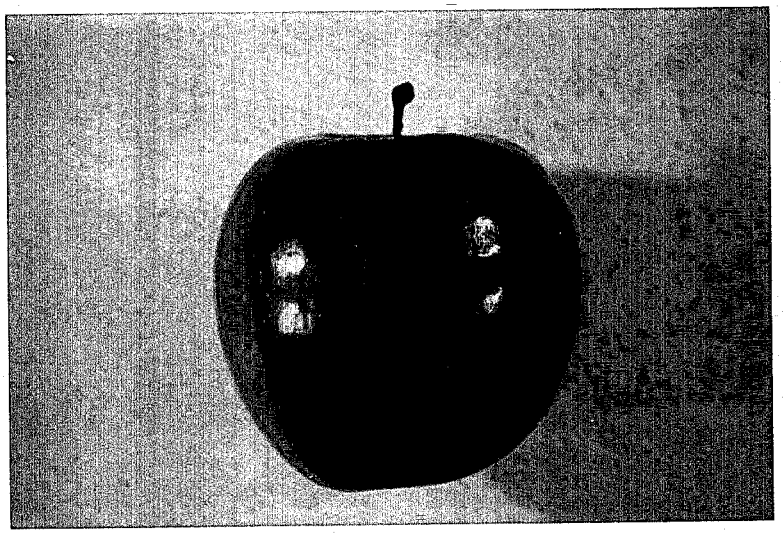
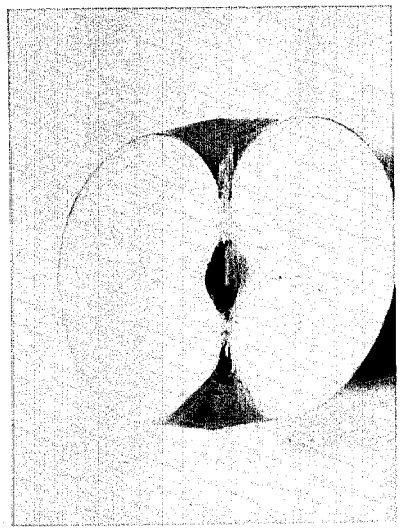
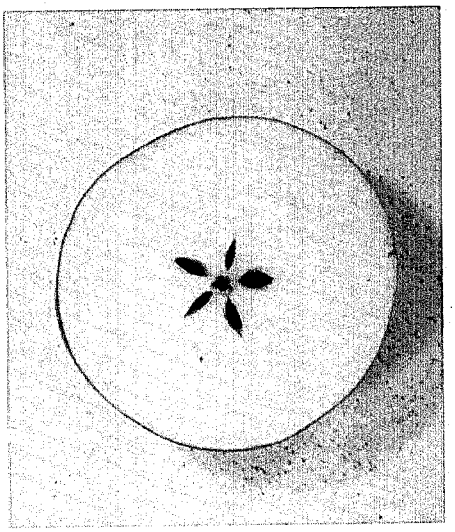

* * * * *